United States Patent
Krieg et al.

(10) Patent No.: US 6,458,213 B1
(45) Date of Patent: Oct. 1, 2002

(54) METHOD AND DEVICE FOR AUTOMATIC CLEANING OF OPTO-ELECTRONIC SENSOR SYSTEMS FOR SUBSTANCE ANALYSIS

(75) Inventors: Gunther Krieg, Im Rennich 12, D-76227 Karlsruhe (DE); Karl Koukolitschek, Karlsruhe (DE); Wilfried Maier, Sulzfeld (DE)

(73) Assignee: Gunther Krieg, Karlsruhe (DE)

( * ) Notice: Subject to any disclaimer, the term of this patent is extended or adjusted under 35 U.S.C. 154(b) by 0 days.

(21) Appl. No.: 09/550,315

(22) Filed: Apr. 14, 2000

(30) Foreign Application Priority Data

Apr. 19, 1999 (DE) .......................................... 199 17 632

(51) Int. Cl.[7] ................................................ G02B 7/00
(52) U.S. Cl. ........................... 134/2; 134/34; 359/509; 356/433; 356/229; 356/239.2; 356/239.7; 356/239.8
(58) Field of Search .............................. 134/2, 10, 18, 134/24, 34; 359/507, 509; 356/433, 229, 239.1, 239.2, 239.7, 239.8, 394

(56) References Cited

U.S. PATENT DOCUMENTS

| | | | | |
|---|---|---|---|---|
| 4,187,868 A | * | 2/1980 | Rudolphi | .................... 134/184 |
| 4,435,093 A | * | 3/1984 | Krause et al. | ............... 374/129 |
| 4,541,277 A | * | 9/1985 | Starnes, Jr. | ................ 73/432 R |
| 5,173,738 A | * | 12/1992 | Bieri | .......................... 356/124 |
| 5,560,060 A | * | 10/1996 | Dausch et al. | .................. 8/158 |
| 5,563,737 A | | 10/1996 | Kamrat | |
| 5,647,914 A | * | 7/1997 | Goto et al. | .................... 134/10 |
| 5,812,270 A | | 9/1998 | Paris | |
| 5,828,458 A | | 10/1998 | Bull | |
| 5,837,063 A | * | 11/1998 | Klug | .............................. 134/6 |
| 5,879,626 A | * | 3/1999 | Watterson et al. | ............. 422/62 |

OTHER PUBLICATIONS

U.S. Statutory Invention Registration, H376, Bremer, Dec. 1987.*

* cited by examiner

Primary Examiner—Randy Gulakowski
Assistant Examiner—J. Smetana
(74) Attorney, Agent, or Firm—Paul Vincent

(57) ABSTRACT

The invention concerns a method and device for automatic cleaning of opto-electronic measuring systems used in process-technology for the analysis of substances in liquids and gases by means of optical absorption and fluorescence. The method is characterized in that the soiling degree is detected by the opto-electronic sensor system itself and, with predetermined soiling degree, a cleaning liquid cleans the soiling-sensitive optical components and detects the residual soiling, which is then evaluated quantitatively and compensated for in the signal analysis.

13 Claims, 3 Drawing Sheets

METHOD AND DEVICE FOR AUTOMATIC CLEANING OF OPTO-ELECTRONIC SENSOR SYSTEMS FOR SUBSTANCE ANALYSIS

This application claims Paris Convention priority of DE 199 17 632 filed Apr. 19, 1999 the complete disclosure of which is hereby incorporated by reference.

BACKGROUND OF THE INVENTION

Conventional opto-electronic sensor systems for the analysis of substances, e.g. using absorption or fluorescence measurements, have the decisive advantages of selectivity, high sensitivity and the possibility of rapid detection of the respective types and concentrations of substances of interest in liquid, gaseous and solid substance mixtures. Linked with these decisive advantages, however, is the disadvantage that important optical components become soiled, such as e.g. optical measuring cells, optical windows, optical radiation sources and optical sensors. This can lead to measurement errors or total failure of the measurement. Prior art discloses various methods and devices, such as e.g. the multi-wavelength method using one or more reference wavelengths according to the patents P 40 30 959, P 40 30 960, EP 91 102 499, and DE 198 494 847. To compensate for the soiling effect, radiation of different wavelengths is transmitted through the substance mixtures and radiation emitted directly by the radiation sources, at the respective time, is detected by a reference sensor and taken into consideration for evaluating the signal (e.g. see the patents DE 36 15 259, P 41 38 419, EP 0383 072).

All of these methods meet practical limitations, since so-called non-gray soiling leads to spectral disturbances which cannot be completely eliminated by the conventional compensation methods and since severe soiling, which occurs in practice, can weaken the light intensities of the various beams to such an extent that the residual light is no longer sufficient for the measurement. This occurs e.g. unavoidably with measurement of isopropanol or isopropanol additive mixtures in the fountain solution of offset printing machines, since the salt content of the paper to be printed, suspended matter from the paper, foreign substances from the paint, chemical additives etc. contaminate the liquid to be measured. This falsifies the optical measurement and eventually prevents carrying it out.

Corresponding effects also occur if one tries to measure the substances of interest in the gas located above the liquid phase, i.e. in the so-called "headspace", since the aerosols generated by the motion of the fountain solution also contain the above-mentioned contaminating and disturbing substances which deposit on the surfaces of the optical components, even when fine pore filters are used.

It is therefore the underlying purpose of the present invention to automatically eliminate the physically unavoidable deposit of soiling or disturbing substances on optical components of sensor systems for the quantitative measurement of the concentrations of the substances contained in liquids or gases and solids, to guarantee correct and interference-free measurement at all times. This methodical measurement is difficult since, in particular, the processing technology must not be disturbed. In particular, there must be no noticeable interruption in the measurement and subsequent dosing processes e.g. of isopropanol or additives. Furthermore, effects due to physically unavoidable residual soiling, which can vary with time depending on the type of soiling, must not distort the measurements.

SUMMARY OF THE INVENTION

Up to this point in time, this difficult object could be solved e.g. neither in offset printing nor in many other practical applications, due to 100% automation requirements, i.e. without any manual operation. The present invention achieves this goal with the cyclic use of cleaning substances and combined application of reference liquids. The invention also provides for timed triggering of the above-mentioned procedures, controlled by the opto-electronic sensor system for substance analysis and with the control of valves for activating the cleaning and reference liquid circuits. These circuits are hermetically sealed with respect to one another and from the process circuit, e.g. the fountain solution circuit of an offset printing machine.

Individual embodiments are described in more detail below for illustration of the present invention.

DESCRIPTION OF THE PREFERRED EMBODIMENT

Figure 1:
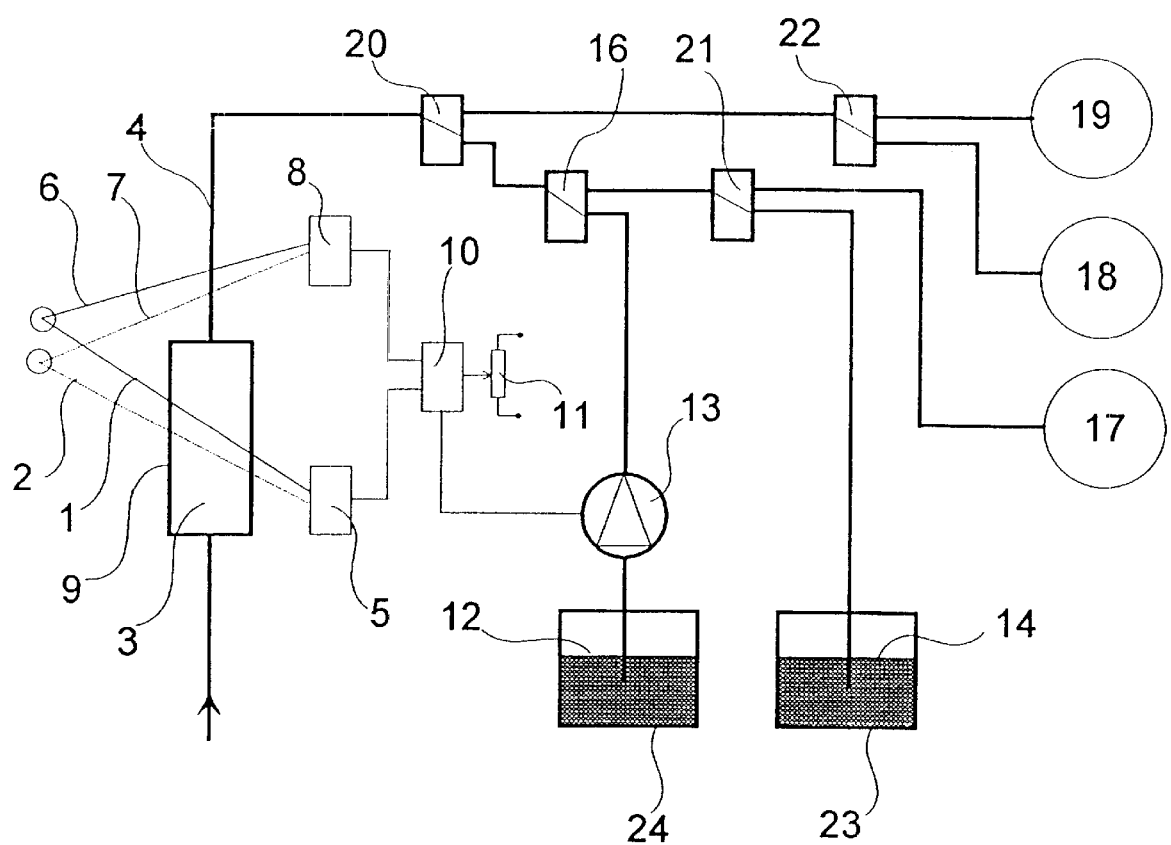
FIG. 1 shows an exemplary embodiment of an opto-electronic sensor system for substance analysis in liquid mixtures using the fully automatic cleaning and reference liquid system for the case of isopropanol concentration determination in the fountain solution of offset printing machines.

In accordance with FIG. 1, a measuring beam 1 and a reference beam 2 pass through the measuring cell 3, continuously flushed by the process liquid 4 to be examined, and are incident on a common measuring sensor 5 using conventional process absorption spectrometry. In addition, a partial measuring beam 6 and a partial reference beam 7 are detected by a reference sensor 8 originating from the same production charge as the measuring sensors. The signals from the measuring sensor 5 and the reference sensor 8 are converted in a conventional manner, e.g. using an analog circuit 10 or e.g. a microprocessor (neither shown in FIG. 1), into the respective concentration signal. This could represent the concentration of isopropanol in the fountain solution mixture of an offset printing machine. When the inner wall 9 is excessively dirtied, the intensity of the reference beam 2 drops below a threshold predetermined by e.g. a threshold value setting means 11. A cleaning circuit is then activated to transport a cleaning liquid 12 through the measuring cell 3 using a feed pump 13. The cleaning liquid 12 may contain an alkaline substance, an acid, or a detergent. The duration of the cleaning process depends either on the process requirements, utilizing interruptions in the measurement and dosing process, or by switching on or off the cleaning process when defined limits for the intensity of the reference beam 2 are exceeded or fallen below. It is difficult to calculate the efficiency of the cleaning process in advance, i.e. since, in general, undefined residual soiling cannot be avoided following a respective cleaning. The status of the soiling is therefore detected in accordance with the present Invention by subsequent rinsing of the measuring cell 3 with a reference liquid 14 and evaluation of the light intensities transmitted by the measuring beam 1 and the reference beam 2. For measurement of the isopropanol concentration or substitute material concentration in the fountain solution of offset printing machines, a reference measurement is carried out using water as the reference liquid 14, which is directly extracted from the respective water circuit 17 via valves 16, 21. If this measurement does not yield an isopropanol concentration of 0.0% a Vol., the sensor system readjusts automatically to this value by offset correction. In addition to or instead of water (which is normally available in regulation processing), other reference liquids, such as isopropanol/water mixtures of conventional concentration can also be used for calibration. The various circuits, i.e. the process circuit 18, the water or reference circuit 17, and the dosing circuit 19 are separated from one another via electromagnetically controlled valves 16, 20, 21, 22 to guarantee, at all times, that the liquid of one circuit is not soiled by the liquids of the two other circuits. The cleaning liquid and the reference liquids are contained in different containers 23, 24. The time-switching of the valves 16, 20, 21, 22 is always effected to prevent cleaning agent from entering into the process circuit, the water circuit and the dosing circuit, with excess water being exclusively supplied to the process circuit.

Figure 2:
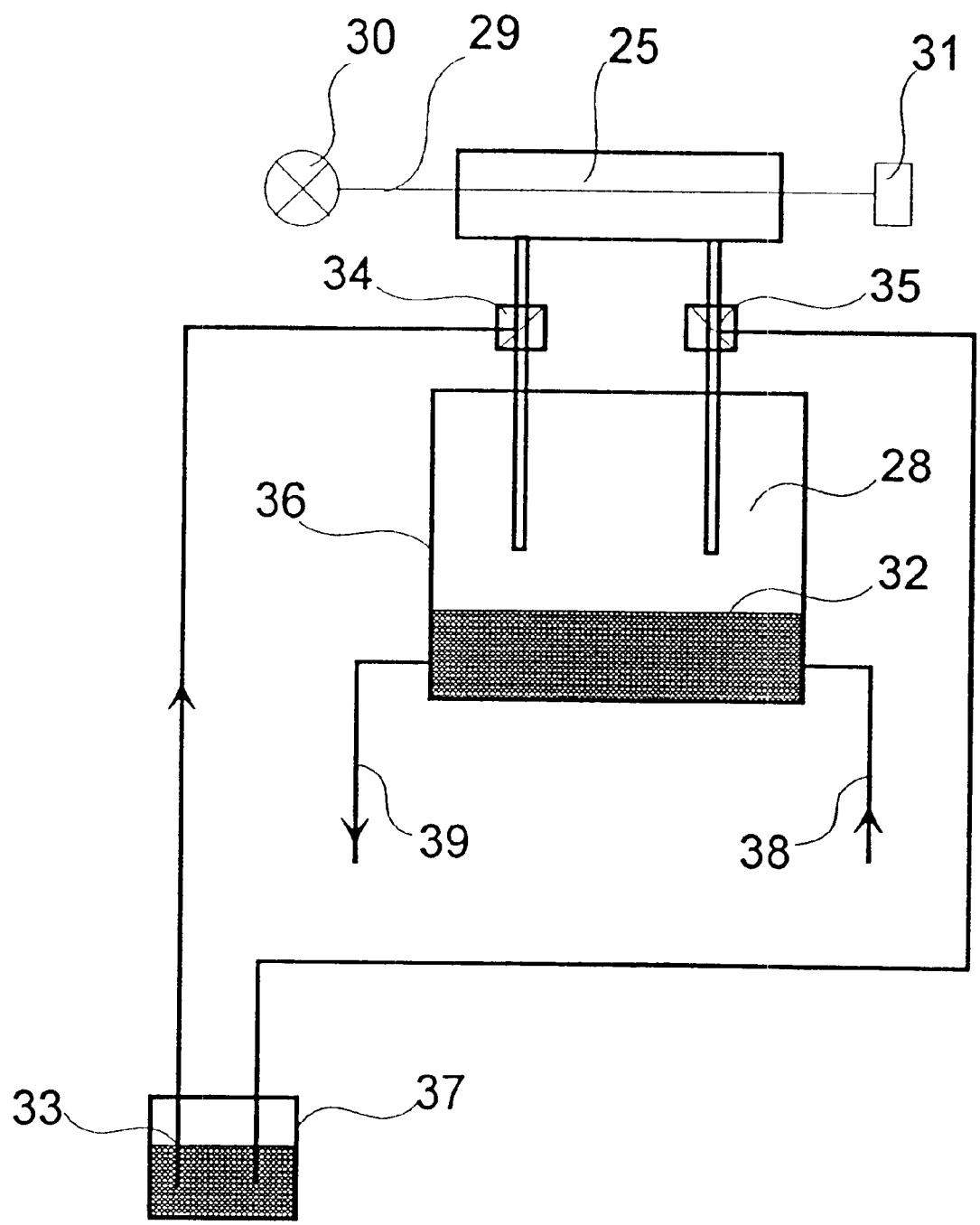
FIG. 2 shows an embodiment of an opto-electronic sensor system, including the reference liquid system, for substance analysis of gaseous mixtures with automatic cleaning of the opto-electronic system components.

In accordance with FIG. 2, the soiling of an opto-electronic substance analysis system for measuring the concentrations of various substance components in the gaseous phase 25, also called "headspace", is kept within narrow limits by means of an automatic cleaning system in accordance with FIG. 1 and operating according to the same method. The gaseous mixture 28, which is representative for the composition of the substance mixture in the liquid 32, is analyzed in a conventional manner using one or more light beams 29 generated by at least one light source 30 whose attenuation is detected by an optical sensor 31. The cyclic cleaning of the optical components is carried out as in FIG. 1 using a cleaning liquid 33 which flows in a conventional manner through the "headspace" 25 via a valve 34. For reference purposes, the measurement cell room 25 can be flooded with water or a reference liquid 33 of a conventional composition, analogously to FIG. 1. As an alternative or additionally, the headspace 25 can be rinsed with a reference gas of a defined composition following cleaning. The process liquid is removed from and returned to the process (not shown) in a circuit via conduits 38, 39. When the cleaning liquid 33 is similar or identical to the process liquid 32, the cleaning liquid can be guided back into the fountain agent container 36. Otherwise, the cleaning liquid is returned to the cleaning container 37 via an additional valve 35.

Figure 3:
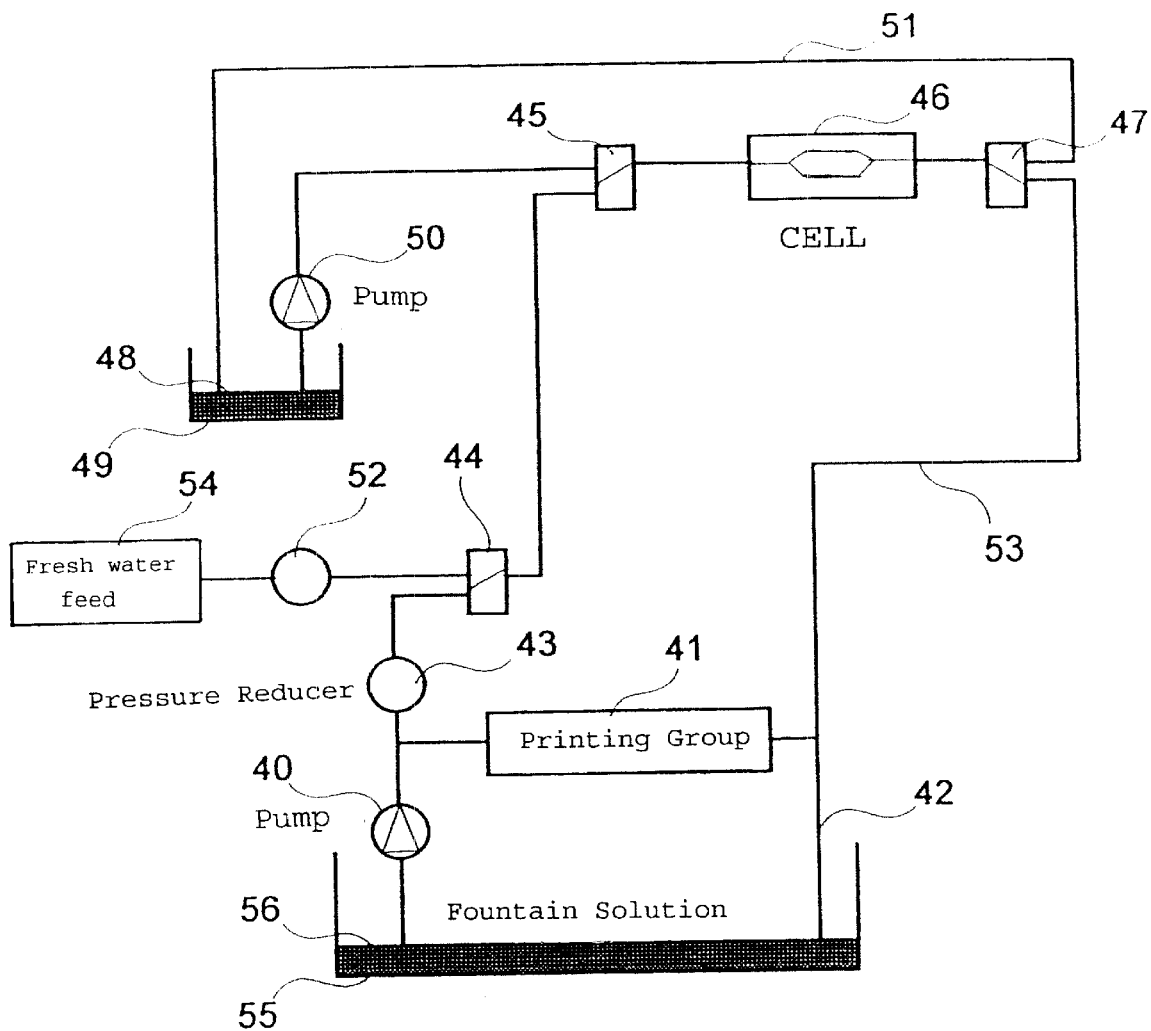
FIG. 3 shows a special exemplary processing technology embodiment of the automatic cleaning or reference system for the offset printing industry.

In accordance with FIG. 3, the fountain agent 56 is transported, via a pump 40, from the fountain agent container 55 to the printing group 41 and returned to the fountain agent container 55 via the return conduit 42. Part of the fountain agent is bypassed to the measuring cell 46 via a pressure reducer 43 and valves 44, 45 and returned, via the valve 47 and the conduit 53, to the fountain agent container 55. When the cleaning process explained in FIG. 1 is triggered after the predetermined threshold value 11 is exceeded, cleaning liquid 48 is transported by a pump 50, via the valve 45, from the cleaning container 49 to the measuring cell 46. Alternatively, fresh water 54, e.g. for rinsing purposes, can be supplied to the measuring cell 46 via a pressure reducer 52 and valves 44, 45 and transported to the process circuit 42 via the return conduit 53.

What is claimed is:

1. A method for automatic cleaning of an opto-electronic sensor system for substance analysis of liquid and gaseous substance mixtures utilizing optical absorption and fluorescence, the method comprising the steps of:

a) monitoring, through detection by the opto-electronic sensor system itself, a degree of soiling;

b) comparing said degree of soiling to a predetermined, stored degree of soiling value;

c) repeating steps a) and b) a plurality of times; and d) automatically cleaning optical surfaces of the sensor system, which are susceptible to soiling, with a cleaning liquid when said degree of soiling exceeds said predetermined, stored value, wherein step a) comprises the step of flooding a headspace measuring room with a cleaning liquid for measuring gaseous substance mixtures.

2. The method of claim 1, further comprising the step of adjusting said predetermined, stored value using a threshold value setting means.

3. The method of claim 1, further comprising the step of e) guiding said cleaning liquid back to a cleaning liquid container while avoiding mixing with a process liquid.

4. The method of claim 1, wherein said cleaning liquid is an alkaline substance.

5. The method of claim 1, wherein said cleaning liquid is acid.

6. The method of claim 1, wherein said cleaning liquid contains a detergent.

7. The method of claim 1, further comprising the steps of f) detecting a residual soiling with the opto-electronic sensor system following step d); and g) including said residual soiling in an evaluation of a measurement signal.

8. The method of claim 7, wherein steps f) and g) comprise the steps of detecting said residual soiling with simultaneous presence of a reference medium in an optical path of optical beams.

9. The method of claim 8, wherein a non-soiled substance mixture is used as said reference medium.

10. The method of claim 8, wherein a pure substance of conventional composition is used as said reference medium.

11. The method of claim 8, wherein said reference medium is a liquid.

12. The method of claim 8, wherein said reference medium is a gas or gaseous mixture.

13. The method of claim 8, wherein said reference medium and said cleaning liquid are passed over said optical surfaces of the sensor system which are susceptible to soiling in separate, closed circuits and without mixing.

* * * * *